(12) United States Patent
Milkau et al.

(10) Patent No.: US 11,103,620 B2
(45) Date of Patent: Aug. 31, 2021

(54) HYBRID IMPLANT MADE OF A COMPOSITE MATERIAL

(71) Applicant: Karl Leibinger Medizintechnik GmbH & Co. KG, Mühlheim (DE)

(72) Inventors: Daniel Milkau, Tuttlingen (DE); Frank Reinauer, Emmingen-Liptingen (DE); Tobias Wolfram, Dreieich (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 0 days.

(21) Appl. No.: 16/093,086

(22) PCT Filed: Apr. 11, 2017

(86) PCT No.: PCT/EP2017/058685
§ 371 (c)(1),
(2) Date: Oct. 11, 2018

(87) PCT Pub. No.: WO2017/182333
PCT Pub. Date: Oct. 26, 2017

(65) Prior Publication Data
US 2019/0134272 A1 May 9, 2019

(30) Foreign Application Priority Data

Apr. 19, 2016 (DE) .......................... 102016107223.0

(51) Int. Cl.
*A61L 27/44* (2006.01)
*A61L 27/46* (2006.01)
*A61L 27/54* (2006.01)
*A61L 27/58* (2006.01)

(52) U.S. Cl.
CPC ............. *A61L 27/446* (2013.01); *A61L 27/46* (2013.01); *A61L 27/54* (2013.01); *A61L 27/58* (2013.01); *A61L 2400/18* (2013.01)

(58) Field of Classification Search
CPC .... A61L 27/446; A61L 24/0047; A61L 27/46; A61L 27/54; A61L 27/58; A61L 2400/18; A61P 43/00; A61P 19/08
See application file for complete search history.

(56) References Cited

U.S. PATENT DOCUMENTS

| | | | |
|---|---|---|---|
| 5,433,751 A | 7/1995 | Christel et al. | |
| 6,432,437 B1 | 8/2002 | Hubbard | |
| 7,291,345 B2 * | 11/2007 | Winterbottom | A61L 27/40 424/400 |
| 2003/0153965 A1 * | 8/2003 | Supronowicz | A61C 8/0007 607/116 |
| 2004/0131562 A1 * | 7/2004 | Gower | A61L 31/128 424/57 |
| 2006/0120994 A1 | 6/2006 | Cotton et al. | |
| 2007/0015110 A1 * | 1/2007 | Zhang | A61K 6/887 433/173 |
| 2008/0069852 A1 * | 3/2008 | Shimp | A61L 27/56 424/423 |
| 2008/0206297 A1 | 8/2008 | Roeder et al. | |
| 2009/0149569 A1 * | 6/2009 | Shastri | A61L 27/446 523/113 |
| 2010/0316591 A1 * | 12/2010 | Cotton | A61K 31/765 424/78.37 |
| 2011/0151027 A1 * | 6/2011 | Clineff | A61L 27/12 424/722 |
| 2011/0270407 A1 | 11/2011 | Cougoulic | |
| 2012/0141429 A1 * | 6/2012 | Hass | C12N 5/0654 424/93.7 |
| 2015/0050618 A1 * | 2/2015 | Foss | C23C 14/34 433/201.1 |
| 2015/0071983 A1 | 3/2015 | Bagga et al. | |
| 2015/0289979 A1 | 10/2015 | Gabele et al. | |
| 2017/0281827 A1 * | 10/2017 | Baker | A61L 27/30 |

FOREIGN PATENT DOCUMENTS

| | | |
|---|---|---|
| DE | 693 32 346 T2 | 12/2003 |
| DE | 102004035182 A1 | 2/2006 |
| DE | 102008040782 A1 | 2/2010 |
| EA | 019109 B1 | 1/2014 |
| EP | 2 730 298 A1 | 5/2014 |
| JP | H06-063118 B2 | 8/1994 |

(Continued)

OTHER PUBLICATIONS

Bedilu, A. et al., "Bioactive and Biodegradable Nanocomposites and Hybrid Biomaterials for Sone Regeneration", J. Funct. Biomater. 2012, 3, pp. 432-463.
Fahmy, M. et al,, "Three-Dimensional Bioprinting Materials with Potential Application in Preprosthetic Surgery", J. of Prosthodontics 25 (2016) pp. 310-318.
Basel Sharaf et al: "Three-Dimensionally Printed Polycaprolactone and ?-Tricalcium Phosphate Scaffolds for Bone Tissue Engineering: An In Vitra Study", Journal of Oral and Maxillofacial Surgery., Bd. 70, Nr. 3, Mar. 1, 2012 (Mar. 1, 2012), Seiten 647-656, XP55387670.
Anna Morawska-Chochöl et al: "Gentamicin release from biodegradable poly-1-lactide based composites for novel intramedullary nails", Materials Science and Engineering C., Bd. 45, Dec. 1, 2014 (Dec. 1, 2014).

(Continued)

*Primary Examiner* — Bruce E Snow
*Assistant Examiner* — Melissa A Hoban
(74) *Attorney, Agent, or Firm* — Banner & Witcoff, Ltd.

(57) ABSTRACT

The present invention relates to a (poly)hybrid implant made of one or more composite materials, having a polymer matrix and a ceramic-inorganic and/or inorganic component, wherein the polymer matrix has at least one component, selected from the group PDLLA; PLGA, PCL, HDPE, PE, UHMWPE, PEAK, PEEK, PP, PUR, and the ceramic-inorganic component has at least one calcium-phosphate-based component, preferably selected from the group HAP, $\alpha$-TCP, $\beta$-TCP and $CaCO_3$. In addition, metallic components can also be introduced, preferably, but not exclusively containing elements such as Mg, Fe, Zn or Sr.

18 Claims, No Drawings

(56) References Cited

FOREIGN PATENT DOCUMENTS

| JP | 2008-518669 A | 6/2008 |
| JP | 2015-536724 A | 12/2015 |
| RU | 2122437 C1 | 11/1998 |
| RU | 2327709 C2 | 6/2008 |
| RU | 2338557 C2 | 11/2008 |
| RU | 2533457 C1 | 11/2014 |
| WO | 2006/050119 A2 | 5/2006 |
| WO | 2008/106625 A2 | 9/2008 |
| WO | 2014/123978 A2 | 8/2014 |
| WO | 2014/152113 A2 | 9/2014 |
| WO | 2017/068492 A1 | 4/2017 |

OTHER PUBLICATIONS

Schiller C et al: "Geometrically structured implants for cranial reconstruction made of biodegradable polyesters and calcium phosphate/calcium carbonate", Biomateri, Elsevier Science Publishers BV., Barking, GB, Bd. 25, Nr. 7-8, Mar. 1, 2004 (Mar. 1, 2004).
International Search Report and Written Opinion for PCT/EP2017/058685; dated Jul. 14, 2017.
Nov. 13, 2017—(DE) Office Action—File No. 10 2016 107 223.0.
Mar. 10, 2020—(EP) Examination Report—App 17718348.0.
Jun. 23, 2020—(RU) Request for Substantive Examination—App 2018136147 (with English translation).
Dec. 31, 2020—(CN) First Office Action—App 201780024648.4.
Feb. 9, 2021—(JP) Notification of Reasons for Rejection—App 2018-554727.

* cited by examiner

1

HYBRID IMPLANT MADE OF A COMPOSITE MATERIAL

CROSS-REFERENCE TO RELATED APPLICATIONS

This application is a U.S. National Stage application under 35 U.S.C. § 371 of International Application PCT/EP2017/058685 (published as WO 2017/182333 A1), filed Apr. 11, 2017, which claims the benefit of priority to Application DE 10 2016 107 223.0, filed Apr. 19, 2016. Benefit of the filing date of each of these prior applications is hereby claimed. Each of these prior applications is hereby incorporated by reference in its entirety.

The present invention relates to a hybrid implant made of a composite material.

As related state of the art, for example from DE 102008040782 A1a method of manufacturing medical hybrid implants is known, comprising at least one first component made of metal and/or ceramic and/or plastic material and at least one second component made of plastic material, characterized in that, prior to connecting the components on the surface(s) of the first component at least partially by means of electromagnetic radiation, a surface structure having a microstructure superimposed by a nano-structure is produced and subsequently the second component is applied.

In up-to-date implant technology, the conception of intelligent implants which, apart from their mechanical or support function, are in active interaction with the tissue surrounding the same is increasingly in the focus of development.

When developing said implants, primarily increasing knowledge of the conditions such as e.g. the messenger cascades in traumatized or healing tissue are resorted to in order to design the implants so that around the implant they locally produce a niche climate which is as beneficial as possible to the tissue healing. Said niche climate is due to a biological niche. A biological niche in this context is understood to be the conditions produced by the locally limited interaction of biological, chemical, physical and structural factors or, resp., the environment produced. Hence, a cellular niche on a micro-level is to be understood in this context.

Since the implant usually is to be completely implanted, i.e. without at a later point in time any possibility of an operating surgeon acting on the implant being given, it is especially important for the development of said implants that the characteristics of the implant can be reliably and reproducibly adjusted in advance for producing a defined niche climate.

An implant known from the state of the art which is to produce a niche climate especially beneficial to healing by the release of messengers or factors, for example, is an implant in the form of a small sponge made from collagen soaked with a particular messenger or factor. When such an implant is introduced into a body, the factors contained in the sponge diffuse out of the sponge into the surrounding tissue and thus may promote the healing of the surrounding tissue.

Said implant shows the following drawbacks, however:

If the diffusion of the messenger or factor from the sponge is intended to be ensured for a quite long period of time, it is initially important to soak the sponge with a messenger solution the concentration of which is far above the physiological concentration of said messenger. This will negatively affect the body's own "signaling cascades" and thus will act undefined in time and space and cannot be specifically switched off. In addition, the diffusion of the messenger into the tissue takes place in an uncontrolled manner and therefore not at a uniform rate or concentration over the entire surface of the implant, hence will then negatively affect the efficiency and function. Therefrom dangerous tissue reactions may result which correspond rather to pathological overexpressions of growth or signal molecules than to the body's own regenerative tissue reactions.

At present, it is another drawback that collagen is employed which itself is already present in the body and may act as a messenger. Thus, undesired side-effects may occur due to the function of the collagen in "signaling cascades". This effect may occur especially in tissues having a relatively low intrinsic collagen proportion. Ergo, processes which are actually undesired may be stimulated.

It is an additional drawback that for manufacturing collagen-based implants usually collagen of animal origin, for example equine collagen, is resorted to. Said collagen is subjected, as a natural product, to higher variations of quality than fully synthetic materials, however, which results in variations of quality and, resp., in a less reliable reproduction and, resp., definition of the characteristics of a collagen-based implant.

Moreover, from the state of the art implants are known the composition of which is selected so that the implant acts as neutrally and passively as possible in the body.

One example hereof is the selection of components of an implant for obtaining an as neutral pH value as possible when the implant is decomposed within the body.

However, said implants have no positive effect on the creation of a biological niche beneficial to tissue healing, rather in said implants above all a negative effect of the implant on wound healing is to be avoided or neutralized so that the implant behaves in a biologically passive manner within the body.

Thus, the object underlying the present invention is to provide an implant which reduces or even eliminates the drawbacks known from the state of the art, especially a biological niche beneficial to tissue healing is to be actively generated after implantation by its precisely and reproducibly adjustable characteristics. Accordingly, deliberately any biologically active, protein-based signal molecules are to be renounced, as the biochemical activity thereof cannot be sufficiently controlled in the healing and functional processes and the stability thereof is not defined and, resp., predictable or controlled in the specific spatial structures.

Advantageously, only non-protein-based signal molecules and, resp., messengers and/or non-proteinogenic signal molecules and, resp., messengers are used within the scope of an implant according to the invention. Thus, the entire hybrid implant or poly-hybrid implant preferably is substantially free from proteins, protein-based substances and proteinogenic substances. Especially preferred, the entire hybrid implant or poly-hybrid implant is completely free from proteins, protein-based substances and proteinogenic substances.

This object is achieved by the implant comprising the features of claim 1, especially by a hybrid implant made of composite material having a polymer matrix and a ceramic-inorganic component, wherein the polymer matrix has at least one component which is selected from the group of PDLLA, PLGA, PCL, HDPE, PE, UHMWPE, PEAK, PEEK, PP, PUR and the ceramic-inorganic component has at least one calcium-phosphate-based component which is preferably selected from the group of HAP, α-TCP, β-TCP and $CaCO_3$.

By selecting its components and its geometric configuration a biological activity advantageous for promoting the tissue healing and, resp., an advantageous biological niche is produced.

The core of the invention consists in the fact that the implant is designed as a "poly"-hybrid implant of a composite material and completely consists of artificially synthesized materials. The composite material has a polymer matrix and at least one ceramic-inorganic or at least one inorganic component or different combinations of said materials. Said components are jointly introduced to the finished implant at defined ratios so as to optimally control bone regeneration.

The polymer matrix may consist, depending on the application, of completely biodegradable polymers, partially biodegradable polymers or else non-biodegradable polymers. In this context, mixed and pure polymers are possible.

The following polymers have turned out to be especially advantageous: poly-DL-lactic acid (PDLLA), polylactic-co-glycolic acid (PLGA), polycaprolactone (PCL), high-density polyethylene (HDPE), polyethylene (PE), ultra-high molecular-weight polyethylene (UHMWPE), polyaryletherketone (PEAK), polyetheretherketone (PEEK), polypropylene (PP), polyurethane (PUR).

The ceramic-inorganic component has at least one calcium-phosphate-based (CaP-based) component which is preferably selected from the group of hydroxyapatite (HAP), $\alpha$-tricalciumphosphate ($\alpha$-TCP), $\beta$-tricalciumphosphate ($\beta$-TCP) and calcium carbonate ($CaCO_3$).

By the use of an organic component, the polymer matrix and a ceramic-inorganic or inorganic component the characteristics of the hybrid implant can be adjusted in an enhanced manner.

So, for example, a non-biodegradable polymer matrix for permanently adopting a supporting function may be provided, while by releasing calcium ions, for example, the biodegradable ceramic component positively causes tissue induction by activating chondrocytes and/or osteoblasts, for example.

In such case, the inductive factors, in the present case ions, primarily are not provided in solution so that the highly concentrated solutions of molecules such as growth factors utilized in the state of the art can be dispensed with. Rather, the ions are uniformly released on the entire surface of the implant by degradation of the implant, are solubilized and thus do not increase the concentration of the naturally occurring components over the period of the effect of the implants. This process can be adjusted and optimized by the methods of manufacturing the hybrid or "poly"-hybrid implants.

Hence, the release parameters of the factors such as the release rate or the time course of release can be exactly adjusted by adapting the composition of the components of the implant and the arrangement and, resp., the processing of said components (e.g. compacting, presence of particular components in defined geometries or gradients etc.).

Advantageous further developments of an implant according to the invention are the subject matter of the subclaims and shall be described in detail hereinafter.

It has turned out to be particularly advantageous when the ceramic-inorganic component contains $CaCO_3$ and the $CaCO_3$ preferably contributes about 10% to about 65%, especially preferred about 15% to about 35%, especially about 15% to about 25% or about 25% to about 35% or about 50% to about 65% percentage by weight to the total mass of the hybrid implant.

$CaCO_3$ in this context serves as degradation accelerator in degrading particular biodegradable polymers and, in addition, acts as an osteo-conductive substance which promotes tight ingrowing of newly formed tissue into an implant. This is especially desirable when the polymer matrix of the hybrid implant consists at least partially of non-biodegradable polymers and thus forms a permanent scaffold structure for the ingrowing tissue. This helps to bring about a new and innovative option of controlling the implant-tissue reaction during new tissue formation as to quantity and space.

$CaCO_3$ may be present as substantially spherical particles, the spherical particles comprising at least one group of spherical particles having a diameter selected from the range of about 10 µm-about 200 µm, especially from the ranges of about 10 µm-about 15 µm; about 20 µm-about 25 µm; about 30 µm-about 45 µm; about 100 µm-about 200 µm. In other words, all $CaCO_3$ particles may have the same diameter or $CaCO_3$ may be present in the form of particles having differently large diameters. The respective selected diameters thus are always deliberately selected or adjusted in advance.

In addition, the $CaCO_3$ particles may have a specific surface modification, e.g. for obtaining a lipophilic or hydrophilic surface, and/or may have a defined topography. Even other particles, which are not $CaCO_3$ particles, or any other components of an implant according to the invention including the polymer matrix may show such surface modification and/or topography.

In addition, an implant according to the invention may also include metallic components, especially at least one out of the metals of magnesium, iron, zinc and strontium. Of course, a mixture is also possible. Said metallic components offer further options of adjusting the characteristics of the implant for producing a particular biological niche. Preferably, the metallic components contribute about 5%-about 15% to the total mass of the hybrid implant.

For example, the metallic components may be provided as particles, fibers or chips, the properties of which in turn may influence, in the case of at least partially biodegradable implants, the degradation of the implant and may also act on the surrounding tissue.

Said metallic components are usually employed in the form of particles. The shaping of the particles may be structured irregularly, substantially spherically or substantially fibrous or substantially twisted or substantially helically.

Furthermore, the completely or non-completely resorbable implant may have a specific "scaffold" structure. Said scaffold structures promote the growth of tissue around and into the implant.

Said scaffold structure may advantageously include hollow structures. Said hollow structures are preferably interconnecting and have diameters of about 100 µm about 800 µm. The configuration of the hollow structures may be adapted to specific applications. By the use of particular production technologies, such as e.g. particular 3D printing methods, hollow structures having a technically exactly defined and adjustable size and distribution or arrangement can be formed. For this purpose, initially one component may be utilized (either polymer or ceramic or inorganic component), subsequently the second component and possibly further components are formed around the primary support and hollow structure.

Said scaffold structure may be formed exclusively by the polymer matrix, but also a compound of a polymer matrix and an inorganic-ceramic component may act as scaffold structure.

By the application-specific design of the implants, especially the structural configuration and chemical composition thereof, spatial niches are enabled to be optimally utilized for endogenous buildup of body tissue.

In order to additionally contribute actively to the production of said biological niche, the hybrid implant may further contain tissue-inductive and/or tissue-conductive factors, especially non-protein-based chemical messengers and/or ions or also antibiotic agents.

Another advantage of the hybrid implant according to the invention consists in the fact that the implant can be manufactured by a sinter-less 3D additive method at a relatively low temperature, i.e. between room temperature (about 25° C.) and about 250° C.

Conventional implants usually are subjected to a sintering step after manufacture so as to obtain the desired mechanical characteristics of the implant. However, when manufacturing the implant according to the invention, due to the properties of the starting materials used the necessity of sintering is removed, thus causing the manufacturing method to be shortened and facilitated.

Advantageously, an implant according to the invention is manufactured in an additive three-dimensional (3D) method. As a possible 3D manufacturing method, especially the methods exemplified in the following are advantageous:

3D printing with powder (3DP), selective laser sintering (SLS), selective heat sintering (SHS), selective laser melting (SLM), electron beam melting (EBM), fused deposition modeling (FDM), fused filament fabrication (FFF), stick deposition molding (SDM), multi-jet modeling (MJM), stereo-lithography (STL or else SLA), scan-LED method (SLT) as further development of classical stereolithography, film transfer imaging (FTI), digital light processing (DLP), polyjet laminated object modeling (LOM) or film laminating 3D printing, selective deposition lamination (SDL).

Particular processes have to be carried out under protective gas, e.g. argon or nitrogen.

Basically, an implant according to the invention can also be manufactured in a subtractive method, however, in which initially a starting plate or a starting block is produced from the starting materials in the desired amounts and, resp., with the desired substance composition, for example by pressing, which starting block then can be further machined, for example.

The versatility of the applications of the implant according to the invention is increased by the fact that the implant material can be machined both additively and subtractively and thus also the implant can be produced both by an additive method and by a subtractive method.

An advantageous embodiment of an implant according to the invention is a completely biodegradable implant containing $CaCO_3$. The $CaCO_3$ contributes about 15% to about 25% to the total mass of the hybrid implant. The polymer matrix includes PDLLA, PCL or PLGA or a mixture of said polymers.

In addition, the hybrid implant contains Mg particles or alloys such as e.g. the magnesium alloy WE43 or MgCa, having a percentage by weight relative to the total mass of about 5%-about 15%. $CaCO_3$ is provided in particle shape. $CaCO_3$ particles have a diameter of about 10 μm about 15 μm and are approximately spherical.

The implant in addition has a scaffold structure including hollows having a diameter of about 300 μm about 450 μm.

It is noted that the invention thus relates to an implant which is completely or partially biodegradable.

The invention claimed is:

1. A hybrid implant made of a composite material comprising a polymer matrix and a ceramic-inorganic component, wherein
   the polymer matrix has at least one component selected from the group of PDLLA, PLGA, PCL, HDPE, PE, UHMWPE, PEAK, PEEK, PP, and PUR;
   the ceramic-inorganic component contains biodegradable $CaCO_3$ as a polymer degradation accelerator, wherein degradation of the hybrid implant uniformly releases calcium ions as an inductive factor on the entire surface of the hybrid implant, and wherein the $CaCO_3$ is present as substantially spherical particles.

2. The hybrid implant according to claim 1, wherein the $CaCO_3$ contributes between 15%-65% percentage by weight to the total mass of the hybrid implant.

3. The hybrid implant according to claim 1, wherein the spherical particles comprise at least one group of spherical particles having a diameter selected from 10 μm-15 μm, 20 μm-25 μm, 30 μm-45 μm, or 100 μm-200 μm.

4. The hybrid implant according to claim 3, wherein the spherical particles on their surface show a defined topography.

5. The hybrid implant according to claim 3, wherein the spherical particles on their surface show a hydrophilic surface modification.

6. The hybrid implant according to claim 3, wherein the spherical particles on their surface show a lipophilic surface modification.

7. The hybrid implant according to claim 1, wherein the hybrid implant is formed as a scaffold structure for tissue conduction having a diameter of 100 μm-800 μm.

8. The hybrid implant according to claim 1, wherein the hybrid implant additionally contains tissue-inductive and/or tissue-conductive factors.

9. The hybrid implant according to claim 1, prepared by a sinter-less 3D additive method at a temperature between room temperature and about 250° C.

10. The hybrid implant according to claim 1, prepared by subtractive removal of a starting material.

11. The hybrid implant according to claim 1, wherein the $CaCO_3$ contributes between 15%-25% percentage by weight to the total mass of the hybrid implant.

12. The hybrid implant according to claim 1, wherein the $CaCO_3$ contributes between 25%-35% percentage by weight to the total mass of the hybrid implant.

13. The hybrid implant according to claim 1, wherein the $CaCO_3$ contributes between 50%-65% percentage by weight to the total mass of the hybrid implant.

14. The hybrid implant according to claim 1, wherein the hybrid implant is formed as a scaffold structure for tissue conduction having a diameter of 300 μm-450 μm.

15. The hybrid implant according to claim 1, wherein the hybrid implant further comprises non-proteinogenic chemical messengers and/or ions, and/or other active agents.

16. The hybrid implant according to claim 1, wherein the composite material further comprises at least one metallic component.

17. The hybrid implant according to claim 16, wherein the at least one metallic component shows an irregular shaping or is configured to be substantially spherical, fibrous, twisted or helical.

18. The hybrid implant according to claim 16, wherein the at least one metallic component is at least one selected from the group consisting of magnesium, iron, zinc, and strontium.

* * * * *